US006713245B2

(12) United States Patent
Koopmans et al.

(10) Patent No.: US 6,713,245 B2
(45) Date of Patent: *Mar. 30, 2004

(54) METHODS FOR STORING NEURAL CELLS SUCH THAT THEY ARE SUITABLE FOR TRANSPLANTATION

(75) Inventors: Jan Koopmans, University of Groningen (NL); Douglas B. Jacoby, Wellesley, MA (US); Jonathan Dinsmore, Brookline, MA (US)

(73) Assignees: Diacrin, Inc., Charlestown, MA (US); University Hospital Groningen (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 38 days.

(21) Appl. No.: 09/110,772

(22) Filed: Jul. 6, 1998

(65) Prior Publication Data

US 2002/0102239 A1 Aug. 1, 2002

(51) Int. Cl.⁷ ................................................. C12N 5/00

(52) U.S. Cl. .......................... 435/1.1; 435/1.3; 435/374; 436/18; 424/93.7

(58) Field of Search .......................... 435/1.1, 1.3, 374; 436/18; 424/93.7

(56) References Cited

FOREIGN PATENT DOCUMENTS

WO    WO 93/01275    * 1/1993

OTHER PUBLICATIONS

Calvet, M.C. et al. (1996) "Gaba–Ergic Neurons In Cultures of Freeze–Stored Embryonic Rat Nervous Tissues: A Morphometric Analysis Using Immunocytochemistry", Society for Neuroscience, vol. 22.*

Cameron, D.F. et al. (1997) "Post–Thaw Viability And Functionality of Cryopreserved Rat Fetal Brain Cells Cocultured With Sertoli Cells", Cell Transplantation, vol. 6, No. 2, pp. 185–189.*

Chanuad, Cheryl M. et al. (1987) "Growth of Neural Transplants in Rats: Effects of Initial Volume, Growth Potential, And Fesh Vs Frozen Tissues" Neuroscience Letters, vol. 80, pp. 127–133.*

Collier, Timothy J. et al. (1993) "Cryopreservation And Storage of Embryonic Rat Mesencephalic Dopamine Neurons For One Year: Comparison to Fresh Tissue In Culture And Neural Grafts", Brain Research, vol. 623 pp. 249–256.*

Collier, Tomothy J. et al. (1987) "Intracerebral Grafting And Cryopreserved Primate Dopamine Neurons" Brain Research, vol. 436 pp. 363–366.*

Collier, T.j. et al. (1988) "Cryopreservation Of Fetal Rat And Non–Human Primate Mesencephalic Neurons: Viability In Culture And Neural Transplantation" Progress in Brain Research, vol. 78 pp. 631–636.*

Dong, J.F. et al. (1995) "Recovery Of Cellular Activity In Cryopreserved Human Foetal Brain Tissue" Restorative Neurology and Neuroscience, vol. 7 pp. 217–224.*

Dong, J.F. et al. (1993) "Susceptibility of Human Foetal Brain Tissue To Cool– and Freeze– Storage", Brain Research, vol. 621 pp 242–248.*

Fang, Jun et al. (1992) "Cryopreservation Of Embryonic Cerebral Tissue of Rat", Cryobiology, vol. 29 pp. 267–273.*

Frodl, Eva M. et al. (1995) "Effects Of Hibernation Or Cryopreservation On The Survival And Integration Of Striatal Grafts Placed In The Ibotenate–Lesioned Rat Caudate–Putamen", Cell Transplantation, vol. 4, No. 6. pp. 571–577.*

Frodl, Eva M. et al. (1994) "Human Embryonic Dopamine Neurons Xenografted To The Rat: Effects Of Cryopreservation And Varying Regional Source Of Donor Cells On Transplant Survival, Morphology And Function" Brain Research, vol. 647 pp 286–298.*

Gage, Fred H. et al. (1985) "Rat Fetal Brain Tissue Grafts Survive And Innervate Host Brain Following Five Day Pregraft Tissue Storage", Neuroscience Letters, vol. 60, pp. 133–137.

Humpel, Christian et al. (1994) "Human Fetal Cortical Tissue Fragments Survive Grafting Following One Week Storage at +4°C." Cell Transplantation, vol. 3, No. 6, pp. 475–479.

Jensen, Steen et al. (1984) "Intraocular Grafts of Fresh and Freeze–Stored Rat Hippocampal Tissue: A Comparison of Survivability And Histological And Connective Organization" The Journal of Comparative Neurology, vol. 227, pp. 558–568.

Kamo, H. et al. (1986) "Functional Recovery In A Rat Model Of Parkinson's Disease Following Transplantation Of Cultured Human Sympathetic Neurons" Brain Research, vol. 397 pp. 372–376.

Kawamoto, Jerroylynn C. et al. (1986) "Cryopreservation Of Primary Neurons For Tissue Culture" Brain Research, vol. 384 pp. 84–93.

(List continued on next page.)

*Primary Examiner*—Leon B. Lankford, Jr.
(74) *Attorney, Agent, or Firm*—Lahive & Cockfield, LLP; Giulio A. DeConti, Jr., Esq.; Megan E. Williams, Esq.

(57) ABSTRACT

The instant methods pertain to an improved methods for storing neural cells, preferably dissociated neural cells, prior to their use in transplantation and to the cells obtained using such methods. One embodiment pertains to methods for storing the neural cells in medium lacking added buffer or added protein, other embodiments feature neural cells which are maintained at 4° C. prior to cryopreservation and have comparable viability and/or functionality to freshly harvested cells. In addition, methods for storing and/or transplantation of porcine neural cells are described.

20 Claims, No Drawings

OTHER PUBLICATIONS

Kontur, P. J. et al. (1993) "Tryosine Hydroxylase Immunoractivity And Monoamine And Metabolite Levels in Cryopreserved Human Fetal Ventral Mesencephalon" Experimental Neurology, vol. 121, pp. 172–180.

Kordower, Jeffrey et al. (1995) "Neuropathological Evidence Of Graft Survival And Striatal Reinnervation After The Transplantation of Fetal Mesencephalic Tissue In A Patient With Parkinson's Disease" The New England Journal of Medicine, Vo. 332, No. 17, pp. 1118–1124.

Kupsch, Andreas et al. (1994) "Neural Transplantation, Trophic Factors And Parkinson's Disease", Life Sciences, vol. 55, Nos. 25/26, pp. 2083–2095.

Nikkhah, Guido et al. (1995) "Preservation Of Fetal Ventral Mesencephalic Cells By Cool Storage: In–Vitro Viability And TH–Positive Neuron Survival After Microtransplantation To The Striatum", Brain Research, vol. 687, pp. 22–34.

Petite, Didier et al. (1995) "Cryopreserved Neuronal Cells In Long–Term Cultures of Dissociated Rat Cerebral Cortex: Survival And Morphometric Characteristics As Revealed By Immunocytochemistry" Brain Research, vol. 669, pp. 263–274.

Petite, Didier et al. (1997) "Morphometric Characteristics Of Cryopreserved Mesencephalic Dopamine Neurons In Culture" Brain Research, vol. 769, pp. 1–12.

Petite, Didier et al. (1997) "Cryopreserved GABAergic Neurons In Cultures Of Rat Cerebral Cortex And Mesencephalon: A Comparative Morphometric Study With Anti–GABA Antibodies", Brain Research, vol. 747 pp. 279–289.

Ray, Jasodhara et al. (1993) "Proliferation, Differentiation, And Long–Term Culture Of Primary Hippocampal Neurons" Proc. Natl. Acad. Sci. USA, vol. 90, pp. 3602–3606.

Redmond, D.E. et al. (1988) "Cryopreservation, Culture, And Transplantation Of Human Fetal Mesencephalic Tissue Into Monkeys" Science, vol. 242, pp. 768–771.

Remond, Edugene D. et al. (1990) "Fludarabine Monophosphate For Prolymphocytic Leukaemia" The Lancet, vol. 336, pp. 820–822.

Robbins, Richard J. et al. (1990) "Cryopreservation Of Human Brain Tissue", Experimental Neurology, vol. 107, pp. 208–213.

Sabate, Olivier et al. (1995) "Transplantation To The Rat Brain Of Human Neural progenitors That Were Genetically Modified Using Adenoviruses", Nature Genetics, vol. 9, pp. 256–260.

Sauer, Hansjorg et al. (1991) "Effects Of Cool Storage On Survival And Function Of Intrastriatal Ventral Mesencephalic Grafts", Restorative Neurology And Neurosceince, vol. 2, pp. 123–135.

Sauer, H. et al. (1992) "Cryopreservatin, Survival and Function Of intrastriatal Fetal Mesencephalic Grafts In A Rat Model Of Parkinson's Disease", Exp. Brain Res, vol. 90, pp. 54–62.

Sautter, Jurgen et al. (1996) "Methylcellulose During Cryopreservation Of Ventral Mesencephalic Tissue Fragments Fails To Improve Survival And Funciton Of Cell Suspension Grafts" Journal of Neuroscience Methods, vol. 64, pp. 173–179.

Seilhean, D. et al. (1996) "Myelintion By Transplanted Human And Mouse Central Nervous System Tissue After Long–Term Cryopreservation" Acta Neuropathol, vol. 91, pp. 82–88.

Silani, Vincenzo et al. (1988) "Human Neuronal Cell Viability Demonstrated In Culture After Cryopreservation" Brain Research, vol. 473, pp. 169–174.

Spencer, Dennis D. et al. (1992) "Unilateral Transplantation Of Human Fetal Mesencephalic Tissue Into The Caudate Nucleus Of Patients With Parkinson's Disease", The New England Journal of Medicine, vol. 327, No. 22, pp. 1541–1548.

Swett, Jay W. et al. (1994) "Quantitative Estimation Of Cryopreservation Viability In Rat Fetal Hippocampal Cells" Experimental Neurology, vol. 129, pp. 330–334.

Yoshimoto, Yusuke et al. (1993) "Improved Cryopreservative Medium Suitable For The Freeze–Storage And Transplantation Of Fetal Neural Tissues" Restorative Neurology and Neuroscience, vol. 6, pp. 73–81.

Brundin, Patrik et al. "Monitoring of Cell Viability in Suspensions of Embryonic CNS Tissue and its Use as a Criterion for Intracerebral Graft Survival" *Brain Research* 331(2):251–59 (1985).

Cai, R. S. et al. "Cryopreservation and culture of the human fetal brain tissues" *J. Tongji Medical Univ.* 13(3):138–42 (1993). Retrieved online from Medline/STN, Database accession No. 94125473 (abstract).

Yoshimoto, T. et al. "Cool storage of fetal rat brain for neural transplantation" *Brain and Nerve* 44(6):553–57 (1992). Retrieved online from Medline/STN, Database accession No. 93001643 (abstract).

Database Medline [Online] US National Library of Medicine (NLM), Bethesda, M.D. et al "Cool storage of fetal art brain for neural transplantation," retrieved from STN Database Acc. No. 93001643 (Abstr. of No to Shinkei. Brain and Nerve 44(6). 553–7 (Jun. 1992)).

Database Medline [Online] US National Library of Medicine (NLM), Bethesda, M.D. et al. "Cryopreservation and culture of the human fetal brain tissues." retrieved from STN Database Acc. No. 94125473 (Abstr of Journal of Tongji Medical University 13(3):138–142 (1993)).

Brundin, P. et al. "Monitoring of cell viability in suspensions of embryonic CNS tissue and its use as a criterion for intracerebral graft survival" Brain Research 331(2):251–9 (1985).

* cited by examiner

METHODS FOR STORING NEURAL CELLS SUCH THAT THEY ARE SUITABLE FOR TRANSPLANTATION

BACKGROUND OF THE INVENTION

Cellular transplantation is a recently developed biomedical technology for the study and treatment of human diseases characterized by cell dysfunction or cell death. For many such diseases current medical therapies or surgical procedures are either inadequate or nonexistent. Cellular therapy can replace or augment existing tissue to provide restorative therapy for these conditions. Exemplary cell types suitable for transplantation include: neural tissue derived cells, hepatocytes, myocytes, retinal cells, endocrine cells, melanocytes, keratinocytes, and chondrocytes. It has been shown in both animal models and in human studies that engraftment of transplanted cells can successfully reestablish tissue function.

In a specific example, cells derived from neural tissue have been used to affect the course of Parkinson's disease, a disorder characterized by depletion of dopaminergic neurons. In neurotoxin-induced, dopamine deficient monkey and rat animal models, xenogeneic and allogeneic fetal ventral mesencephalon (VM) cell preparations isolated from pigs, rats, or humans have been reported to reverse the movement disorder (see e.g., Kopyov et al. 1992 *Transplantation Proceedings* 24: 547–548; Huffaker et al. 1989 *Exp. Brain Res.* 77:329). Human fetal VM grafts have also been reported to affect the course of Parkinson's disease in man by reinervating the dopamine (DA) depleted host striatum (see e.g., Lindvall et al. 1990 *Science,* 242: 574–577; Lindvall et al. 1994 *Ann. Neurol.* 35: 172–180; Widner et al. 1997 *Ann. Neurol.* 42:95.; Kordower et al. 1995 *New Engl. J. Med* 332:1118).

Nevertheless, current methods of cell transplantation, particularly those which utilize freshly prepared neural tissue, have been hindered by the lack of available cell sources and limited viability of neural cells after preparation. These problems are compounded by the logistical problems involved in ensuring that surgeons, operating rooms, patients, and fresh cells are all available at the same time. Finally, the need to rapidly implant the fresh cells following preparation hinders extensive quality control prior to implantation.

In view of the above, it is desirable to store, and sometimes pool, freshly harvested cells prior to implantation. It would also be desirable to store cells which have been cultured in vitro. Such storage would allow banking, quality control, and other desired procedures and manipulations, either in connection with in vitro analysis or implantation in vivo.

Methods for cell storage prior to transplantation include preserving the tissue by freezing cells ("cryopreservation") (see e.g., Chanaud et al. 1987 *Neurosci. Lett.* 82: 127–133; Collier et al. (1987) 436: 363–366) or by refrigerating the cells at above freezing temperatures ("hibernation") (see e.g., Sauer et al. 1991 *Neurology and Neuroscience* 2: 123–135; Gage et al. 1985 *Neurosci. Lett.* 60: 133–137). However, freezing of fresh neural tissue results in poor viability after thawing and low yield or recovery of cell numbers. Specifically, studies comparing survival of cryopreserved and fresh transplanted tissue have shown dramatic decreases in the survival of cryopreserved grafts as compared to fresh control tissue (see e.g., Jensen et al. 1984 *J. Comp. Neurol.* 227: 558–68). For example, tissue culture experiments have indicated that cryopreservation may lead to decreases in neuronal survival to between one-and two-thirds of fresh control values (see e.g., Collier et al. 1988 *Progress in Brain Research,* 78: 631–6). In particular, human tissue may be more susceptible to damage induced by freezing than rat tissue, which is reflected in poor graft survival and reduction in cell size of the cryopreserved neurons (Frodl et al. 1994 *Brain Research,* 647:286–298).

Storage of tissue in preservative media at temperatures above freezing temperatures (hibernation) can result in high rates of graft survival and function as compared to cryopreserved tissue (see e.g., Sauer et al. 1991 supra.; Kawamoto et al. 1986 *Brain Res.,* 384: 84–93). However, cells cannot be maintained for long periods of time under such conditions. Specifically, cell viability is progressively decreased during hibernation. Within about one week, such losses render the cell population unacceptable for transplantation in vivo.

In addition, prior art methods for freezing and hibernating cells utilize complex media comprising buffers and added protein, sometimes including entirely undefined components, such as serum. However, to minimize toxicity and immunogenicity such additives are not desirable for transplantation into humans and hinder controlled studies of neural cell growth, development and function in vitro.

SUMMARY OF THE INVENTION

This invention solves the problems referred to above by providing methods for storing neural cells without significant decreases in cell viability and/or functionality. Such methods greatly enhance the availability of cells for in vitro analysis and/or transplantation in vivo. Such methods are also useful when pooling of cells is desired.

In one aspect, the invention pertains to a method for storing cells in a cryopreserved state in which fresh or cultured neural cells are suspended in a cryopreservation solution, the temperature of the cell suspension is decreased in a controlled manner to about −196° C. and the cells are maintained in a frozen state.

In another aspect, the invention pertains to a method for storing cells in hibernation in which fresh, cultured, or cryopreserved neural cells are suspended in a hibernation medium which is preferably free of added protein, free of a buffer, or free of added protein and a buffer, and the cell suspension is maintained at temperatures which are above freezing and sufficiently below normal body temperature such that normal physiological cell processes are decreased or halted.

In another aspect, the invention pertains to cultures of cells which have been stored according to a cryopreservation method and/or hibernation method of the invention. Such cells are useful for in vitro growth, development, and analysis as well as for transplantation in vivo.

In another aspect, the invention pertains to methods of implantation which utilize neural cells which have been stored according to the methods disclosed herein.

DETAILED DESCRIPTION OF THE INVENTION

The present invention pertains, inter alia, to improved methods of storing neural cells, preferably dissociated neural cells, prior to their use in transplantation and to the cells obtained using such methods. This invention provides for long-term storage of neural cells without significant decreases in cell viability and/or function. Accordingly, the present invention represents a significant advance over the previous cell storage methods. The instant invention is based, in part, on the discovery that neural cells can be stored and/or frozen in a medium, which lacks any buffer or added protein. In addition, improved methods for storing porcine cells are provided. One aspect of the invention features methods which employ a hibernation step of as long as 3–5 days prior to and/or post freezing (or instead of freezing) while still recovering neural cells suitable for transplantation. The ability to store cells without loss of viability and/or function allows for the separation in time between cell preparation and implantation into a subject. The ability to store cells also enables the pooling of cells from multiple donors and adequate time for quality control assessment of cells and other in vitro analysis.

As used herein, the following terms and phrases shall be defined as follows:

"Storing" includes maintaining neural cells after harvest from a donor and prior to use in transplantation in a subject. The term "storing" is meant to include holding or maintaining cells either above or below freezing.

"Cryopreservation" includes preservation of cells at temperatures below freezing.

"Hibernation" includes preservation of cells at temperatures above freezing and sufficiently below normal physiological temperature such that one or more normal cellular physiological processes are decreased or halted. Preferred hibernation temperatures range between 0 and 4° C., preferably about 4° C.

"Neural cells" includes any differentiated neural cells derived from the nervous system of a human or an animal, preferably the central nervous system. Preferably, neural cells for use in the instant methods have undergone final maturation, but have not sent out projections (e.g., axons). The term "neural cells" includes for example, neural stem cells or neural progenitor cells which have been induced to differentiate into neural cells in vitro and neural stem cells or neural progenitor cells which have differentiated into neural cells in vivo. The term "neural cell" also includes, for example, neurons, astrocytes, and oligodendrocytes. The term "cells" is used interchangeably herein with the term "neural cells". The term "cells" as used herein encompasses both neural cells in the form of tissue (e.g., intact pieces of tissue) and dissociated neural cells, e.g., in the form of a cell suspension.

"Hibernation medium" as used herein, includes any medium which lacks a cryopreservative and is physiologically compatible for storage of a cell at above freezing temperatures, preferably about 4° C.

"Cell suspension" as used herein includes cells in intact pieces of tissue that are contacted with a medium and cells which have been dissociated, e.g., by subjecting a piece of tissue to gentle trituration, which are in contact with a medium.

"Adapted cell suspension" includes a cell suspension that has been stored above freezing, preferably at 40° C., in hibernation medium for about 1 hour–5 days.

"Cryopreservation solution" includes a solution which contains a cryopreservative, i.e., a compound which protects cells against intracellular and/or cell membrane damage as the cells are frozen or thawed. A cryopreservative is identified by enhanced viability and/or functionality of cells in contact with the cryopreservative when compared with cells which are similarly frozen or thawed in the absence of the cryopreservative. Any cryopreservative can be used in conjunction with the instant methods and the term is meant to encompass both intracellular and extracellular cryopreservatives.

"Suitable for transplantation" refers to a cell or a population of cells which is stored, cryopreserved, and/or obtained using any of the instant methods and which are sufficiently viable and/or functional such that a neurological disorder or dysfunction is treated, e.g., one or more symptoms of a neurological disorder or dysfunction are ameliorated or reduced for a period of time following implantation of the cell or population of cells into a subject suffering from a neurological disorder or dysfunction.

In one aspect, the invention pertains to a method for storing a population of fetal porcine neural cells suitable for transplantation comprising: a) contacting a population of porcine neural cells with a hibernation medium to thereby produce a cell suspension; and b) maintaining the cell suspension at about 4° C. to thereby store a population of neural cells suitable for transplantation.

In another aspect the invention pertains to a method for cryopreserving a population of fetal porcine neural cells suitable for transplantation comprising: a) contacting a population of porcine neural cells with a cryopreservation solution to thereby obtain a population of cells for cryopreservation; and b) decreasing the temperature of the population of neural cells for cryopreservation to about $-196°$ C. to thereby cryopreserve a population of neural cells suitable for transplantation.

In yet another aspect, the invention pertains to a method of obtaining a population of fetal porcine neural cells suitable for transplantation comprising: a) contacting a population of porcine neural cells with a cryopreservation solution to thereby obtain a population of cells for cryopreservation; b) decreasing the temperature of the population of neural cells for cryopreservation to about $-196°$ C. to obtain cryopreserved neural cells; c) increasing the temperature of the cryopreserved neural cells to thereby obtain a population of neural cells suitable for transplantation; and d) contacting the population of porcine neural cells suitable for transplantation with a hibernation medium and maintaining the cells at about 4° C. prior to transplantation.

In one embodiment of the invention, the porcine neural cells are ventral mesencephalic cells. In a preferred embodiment, the ventral mesencephalic cells are porcine cells obtained between about days 25 and 28 of gestation. In another embodiment, the porcine cells are spinal cord cells. In another embodiment, the porcine neural cells are striatal cells. In a preferred embodiment, the striatal cells are obtained from a lateral ganglionic eminence of porcine striatum. In another embodiment, the porcine neural cells are cortical cells.

In another embodiment, the invention pertains to a population of porcine neural cells for transplantation prepared according to the instant methods.

In yet another embodiment, the invention pertains to a method for treating a neurological disorder or dysfunction comprising transplanting the population of porcine neural cells obtained using the instant methods into a subject.

In another aspect, the invention pertains to a method for storing a population of human or porcine neural cells suitable for transplantation comprising: a) contacting a population of neural cells with a hibernation medium which medium is free of added protein to thereby produce a cell suspension; and b) maintaining the cell suspension at about 4° C. to thereby store a population of neural cells suitable for transplantation.

In another aspect, the invention pertains to a method for storing a population of human or porcine neural cells suitable for transplantation comprising: a) contacting a population of neural cells with a hibernation medium which medium is free of a buffer to thereby produce a cell suspension; and b) maintaining the cell suspension at about 4° C. to thereby store a population of neural cells suitable for transplantation.

In another aspect, the invention pertains to a method for storing a population of human or porcine neural cells suitable for transplantation comprising: a) contacting a population of neural cells with a hibernation medium which medium is free of added protein and free of a buffer to thereby produce a cell suspension; and b) maintaining the cell suspension at about 4° C. to thereby store a population of neural cells suitable for transplantation.

In another aspect, the invention pertains to a method for storing a population of human or porcine neural cells suitable for transplantation comprising: a) contacting a population of neural cells with a hibernation medium which medium consists of glucose and sodium chloride to thereby produce a cell suspension; and b) maintaining the cell suspension at about 4° C. to thereby store a population of neural cells suitable for transplantation.

In yet another aspect, the invention pertains to a method for cryopreserving a population of human or porcine neural cells suitable for transplantation comprising: a) contacting a population of neural cells with a cryopreservation solution which is free of added protein and which comprises a cryopreservative to thereby obtain a population of cells for cryopreservation; and b) decreasing the temperature of the population of neural cells for cryopreservation to about −196° C. to thereby cryopreserve a population of neural cells suitable for transplantation.

In another aspect, the invention pertains to a method for cryopreserving a population of human or porcine neural cells suitable for transplantation comprising: a) contacting a population of neural cells with a cryopreservation solution which is free of a buffer and which comprises a cryopreservative to thereby obtain a population of cells for cryopreservation; and b) decreasing the temperature of the population of neural cells to about −196° C. to thereby cryopreserve a population of neural cells suitable for transplantation.

In another aspect, the invention pertains to a method for cryopreserving a population of human or porcine neural cells suitable for transplantation comprising: a) contacting a population of neural cells with a cryopreservation solution which is free of added protein and free of a buffer and which comprises a cryopreservative to thereby obtain a population of cells for cryopreservation; and b) decreasing the temperature of the population of neural cells for cryopreservation to about −196° C. to thereby cryopreserve a population of neural cells suitable for transplantation.

In another aspect, the invention pertains to a method for cryopreserving a population of human or porcine neural cells suitable for transplantation comprising: a) contacting a population of neural cells with a cryopreservation solution consisting of glucose, sodium chloride, and a cryopreservative to thereby obtain a population of cells for cryopreservation; and b) decreasing the temperature of the population of neural cells for cryopreservation to about −196° C. to thereby cryopreserve a population of neural cells suitable for transplantation In another aspect, the invention pertains to a method of obtaining a population of human or porcine neural cells suitable for transplantation comprising: a) contacting a population of neural cells with a cryopreservation solution which is free of added protein which comprises a cryopreservative to thereby obtain a population of cells for cryopreservation; b) decreasing the temperature of the population of neural cells for cryopreservation to about −196° C. to obtain cryopreserved neural cells; and c) increasing the temperature of the cryopreserved neural cells to thereby obtain a population of neural cells suitable for transplantation.

In another aspect, the invention pertains to a method of obtaining a population of human or porcine neural cells suitable for transplantation comprising: a) contacting a population of neural cells with a cryopreservation solution which is free of a buffer and which comprises a cryopreservative to thereby obtain a population of cells for cryopreservation; b) decreasing the temperature of the population of neural cells for cryopreservation to about −196° C. to obtain cryopreserved neural cells; and c) increasing the temperature of the cryopreserved neural cells to thereby obtain a population of neural cells suitable for transplantation.

In yet another aspect, the invention pertains to a method of obtaining a population of human or porcine neural cells suitable for transplantation comprising: a) contacting a population of neural cells with a cryopreservation solution which is free of added protein and free of a buffer and which comprises a cryopreservative to thereby produce a population of neural cells suitable for cryopreservation; b) decreasing the temperature of the population of neural cells for cryopreservation to about −196° C. to obtain cryopreserved neural cells; and c) increasing the temperature of the cryopreserved neural cells to thereby obtain a population of neural cells suitable for transplantation.

In still another aspect, the invention pertains to a method of obtaining a population of human or porcine neural cells suitable for transplantation comprising: a) contacting a population of neural cells with a cryopreservation solution consisting of: glucose, sodium chloride, and a cryopreservative to thereby obtain a population of cells for cryopreservation; b) decreasing the temperature of the population of neural cells for cryopreservation to about −196° C. to obtain cryopreserved neural cells; and c) increasing the temperature of the cryopreserved neural cells to thereby obtain a population of neural cells suitable for transplantation.

In certain embodiments of the invention, the neural cells are fetal human cells. In preferred embodiments, the neural cells are human neural stem or neural progenitor cells that have been induced to differentiate in vitro prior to storage using the instant methods.

In other embodiments of the invention, the neural cells are porcine cells. In still other embodiments, the porcine neural cells are ventral mesencephalic cells. In yet other embodiments, the porcine neural cells are porcine spinal cord cells. In still other embodiments, the porcine neural cells are striatal cells. In still other embodiments, the porcine neural cells are cortical cells. In still further embodiments, the porcine cells are porcine neural stem cells or neural progenitor cells. In certain embodiments, the porcine neural stem cells or progenitor cells have been induced to differentiate in vitro prior to storage using the instant methods.

In other embodiments of the invention, the invention pertains to a population of human or porcine neural cells for suitable for transplantation prepared according to the instant methods.

In still other embodiments of the invention, the invention pertains to a method for treating a neurological disorder or dysfunction comprising transplanting a population of human or porcine neural cells stored according to the claimed methods into a subject.

In another aspect, the invention pertains to a method for storing a population of porcine neural cells suitable for transplantation comprising: a) contacting a population of neural cells with a hibernation medium to thereby produce a cell suspension; b) maintaining the cell suspension for at least about 24 hours at about 4° C. in hibernation medium to thereby store a population of neural cells suitable transplantation.

In another aspect, the invention pertains to a method for cryopreserving a population of human or porcine neural cells suitable for transplantation comprising: a) contacting a population of neural cells with a hibernation medium to thereby produce a cell suspension; b) maintaining the cell suspension for at least about 24 hours at about 4° C. in hibernation medium to thereby produce an adapted cell suspension; c) contacting the adapted cell suspension with a cryopreservation solution to thereby obtain a population of cells for cryopreservation; and d) decreasing the temperature of the population of neural cells suitable for cryopreservation to about −196° C. to thereby cryopreserve a population of neural cells suitable for transplantation.

In another aspect, the invention pertains to a method of obtaining a population of human or porcine neural cells for transplantation comprising: a) contacting a population of neural cells with a hibernation medium to thereby produce a cell suspension; b) maintaining the cell suspension for at least about 24 hours at about 4° C. in hibernation medium to thereby produce an adapted cell suspension; c) contacting the adapted cell suspension with a cryopreservation solution to thereby obtain a population of cells for cryopreservation; d) decreasing the temperature of the population of neural cells for cryopreservation to about −196° C.; and e) increasing the temperature of the neural cells to thereby obtain population of neural cells suitable for transplantation.

In certain embodiments the cell suspension is maintained at about 4° C. for about 72 hours. In preferred embodiments the cell suspension is maintained at about 4° C. for at least about 40–48 hours. In more preferred embodiments, the cell suspension is maintained at about 4° C. for at least about 44 hours.

The invention is further described in the following subsections:

Neural Cells

Neural cells useful in the methods of this invention can be fresh cells or may be obtained from in vitro culture.

Preferably, the cells of the invention are of mammalian origin, i.e., are obtained from mammalian subjects (e.g., humans, pigs, or cows). In one embodiment, the cells are bovine. Preferred cells for use in the instant methods are porcine. Other preferred cells are human.

Neural cells can be derived or obtained from a variety of tissues which are selected based, at least in part, on the intended use for the cells, e.g., the particular function to be assessed or clinical indication to be addressed. For example, if the cells are to be used to treat paralysis, it may be desirable to obtain them from the spinal cord of a donor subject. When the cells are intended for implantation into humans with Parkinson's disease, they are preferably derived from a region of the brain giving rise to dopamine-producing cells.

Similarly, the neural cells useful in the methods of this invention may be obtained during various stages of development of the donor subject, including, fetal, juvenile, and adult cells. In general, the particular stage of development is selected based upon the intended use of the cells subsequent to storage and the species of animal from which the cells are derived.

In one embodiment, the cells for use in the present invention are fetal cells. Preferably, the cells are derived from the fetal central nervous system. In another embodiment, the fetal cells are spinal cord cells. In preferred embodiments the fetal cells are ventral mesencephalic cells. In still other preferred embodiments the fetal cells are striatal cells. In yet other preferred embodiments the striatal cells are obtained from a lateral ganglionic eminence of the striatum. In other embodiments, the fetal cells are cortical cells.

Preferably, cells for use in the instant methods are used after they have undergone their final maturation, but before they have sent out projections, e.g., axons. For example, in one embodiment, the fetal human cells are obtained from fetuses ranging in age from 7 to 18 weeks of gestation. In preferred embodiments, fetal human cells are obtained at between 7 and 11 weeks gestation. Fetal human cells for use in the claimed methods are obtained using methods known in the art and as required under the guidelines for use of human tissue (see e.g., DHEW publication OS 1975). In embodiments in which fetal porcine cells are used, preferably the cells are obtained between about days 20 and 115 of gestation, depending on the cell type to be isolated. For example, in certain embodiments, e.g., when the cells are porcine ventral mesencephalic cells, the cells are obtained between about days 25 and 28 of gestation. Preferably the porcine VM cells are used between about days 26 and 27 of gestation. More preferably, the porcine VM cells are used at about 27 days of gestation. In the case of fetal porcine striatal cells, preferably the cells are obtained from a fetus at between about days 30 and 50 of gestation. In more preferred embodiments, the porcine striatal cells are obtained from a fetus between about days 31 and 38 of gestation. In particularly preferred embodiments, the porcine striatal cells are obtained from a fetus between about days 34 and 36 of gestation. In the case of porcine cortical cells, the cells are preferably obtained from a fetus between about days 20 and 30 of gestation. In particularly preferred embodiments, the porcine cortical cells are obtained from a fetus between about days 24 and 28 of gestation.

In certain embodiments, the cells for use in the instant methods are neural stem cells which have been induced to differentiate. In other embodiments, the cells are neural progenitor cells which have been induced to differentiate. Tissue containing stem or progenitor cells can be obtained from mammalian fetuses, juveniles, or from an adult organ donor. In preferred embodiments, stem cells to be used in the instant methods are porcine cells. In other preferred embodiments, stem cells to be used in the instant methods are human cells. In certain embodiments, autologous stem cells from the donor may be obtained, differentiated and cryopreserved using the instant methods.

Neural stem or progenitor cells can be obtained from any area of the central nervous system, including the cerebral cortex, cerebellum, midbrain, brainstem, spinal cord, ventricular tissue, or from areas of the peripheral nervous system, including the carotid body and the adrenal medulla. Methods of obtaining neural progenitor or stem cells are known in the art (see e.g., U.S. Pat. No. 5,753,506; WO97/44442; WO96/04368; WO94/10292; WO94/02593; Gage et al. 1995 *Ann. Rev. Neurosci.* 18:159).

To expand a population of neural cells, (e.g., stem or progenitor cells) the cells can be grown in the presence of trophic factors, such as nerve growth factor, acidic fibroblast growth factor, basic fibroblast growth factor, platelet-derived growth factor, thyrotropin releasing hormone, epidermal growth factor, amphiregulin, transforming growth factor, transforming growth factor β, insulin-like growth factor, or other growth factors using methods known in the art (see, e.g., U.S. Pat. No. 5,753,506, U.S. Pat. No. 5,612, 211, U.S. Pat. No. 5,512,661, WO93/01275; Mehier and Kessler. 1995 *Crit. Rev. Neurobiol.* 9:419).

Neuronal or glial cells can be differentiated from an expanded stem or progenitor cell population by treating the cells by any method known in the art which promotes differentiation of the cells, for example, phorbol esters or various growth factors (See, e.g., U.S. Pat. Nos. 5,750,376; 5,753,506; WO 96/15226; WO 94/02593; WO 96/15224). Alternatively, a surface such as poly-L-lysine can be used to induce differentiation (WO 93/01275). Such differentiated cells can be stored using the instant methods.

In certain embodiments, pieces of tissue are left intact, or stored as fragments, e.g., are not dissociated into individual cells prior to used in the instant methods. In preferred embodiments, the cells to be used in the claimed methods are dissociated, e.g., into individual cells to make a suspension prior to their use in the instant methods. For example, tissue can be dissociated using gentle trituration. Methods of dissociating tissue are known in the art and include the use of flame-polished pasteur pipets of diminishing orifice diameters or a succession of Angio-catheters of diminishing orifice diameters.

Hibernation Conditions

Numerous types of media can be used as hibernation media in conjunction with the instant methods. In preferred embodiments, hibernation media is free of added Ca++. In certain embodiments, medium for hibernating cells is free of added protein and/or free of a buffer. A preferred hibernation medium includes or consists of glucose in a saline solution, e.g., between about 0.2%–0.9% glucose in saline. In preferred embodiments, the hibernation medium includes or consists of about 0.35–0.9% glucose and 0.9% NaCl. In other preferred embodiments, the medium includes or consists of about 0.6% glucose and 0.9% NaCl. In certain embodiments, more complex media can be used, e.g., Hank's balanced salt solution, Dulbecco's minimal essential medium (see e.g., Nikkah et al. 1995 *Brain Research* 687:22), or Eagle's modified minimal essential medium. Another suitable hibernation medium has been described by Kawamoto and Barrett (1986 *Brain Research* 384:84). In certain embodiments it may be desirable to supplement the chosen hibernation medium with additives, for example, added protein (e.g., mammalian serum protein or whole serum (preferably heat inactivated)) buffers (e.g., phosphate buffers, HEPES, or the like) antioxidants, growth factors, KCl (e.g., at about 30 mM), lactate (e.g., at about 20 mM), pyruvate, $MgCl_2$ (e.g., at about 2–3 mM), sorbitol (e.g., at about 300 mM) or other additives as are well known in the art (e.g., as taught by Kawamoto and Barrett supra).

In certain embodiments, the cells of the invention are hibernated at about 0–37° C., preferably about 40° C. In certain embodiments, cells are maintained at about 4° C. in hibernation medium prior to freezing or use. In other embodiments the cells of the invention are maintained at about 4° C. in hibernation medium post freezing. In still other embodiments, the cells of the invention are maintained at about 4° C. in hibernation medium without freezing. In certain embodiments, the cells of the invention are maintained in hibernation medium at about 4° C. for at least about 1 hour to 5 days prior to freezing, post freezing or prior to use in transplantation. In other embodiments, the cells of the invention are maintained in hibernation medium at about 4° C. for at least about 12–72 hours prior to freezing, post freezing or prior to use in transplantation. In certain embodiments the cells are maintained at 4° C. in hibernation medium for at least about 24 hours prior to freezing, post freezing or prior to use in transplantation. In a more preferred embodiment, the cells are maintained in hibernation medium from at least about 40–48 hours at about 4° C. prior to freezing, post freezing or prior to use. In a particularly preferred embodiment, the cells are maintained in hibernation medium for at least about 44 hours at about 4° C. prior to freezing, post freezing or prior to use.

Freezing Conditions

Any cryopreservative known in the art can be used in a cryopreservative solution of the instant invention. In preferred embodiments, cryopreservation solutions of the present invention include intracellular cryopreservatives e.g., dimethylsulfoxide (DMSO), various diols and triols (e.g., ethylene glycol, propylene glycol, butanediol and triol and glycerol), as well as various amides (e.g., formamide and acetamide). However, extracellular cryopreservatives e.g., phosphomono and phosphodiester catabolites of phosphoglycerides (EP 0 354 474), polyvinylpyrrolidone (Fang and Zhong 1992 *Cryobiology* 29:267), or methylcellulose (e.g., at 0.1%, see e.g., Sautter et al. 1996 *J. of Neuroscience Methods.* 64:173) can also be used alone or in conjunction with an intracellular cryopreservative.

In preferred embodiments, DMSO is used as the cryopreservative. DMSO can be used at a wide range of concentrations (see e.g., Silani et al. 1988 *Brain Research* 473:169). In preferred embodiments, DMSO is used at a final concentration of about 4% to about 10%. In more preferred embodiments the concentration of DMSO ranges from about 7% to about 10%. In particularly preferred embodiments the concentration of DMSO is about 7%.

In certain embodiments, the cryopreservative is added to the cells in a stepwise manner in order to gradually increase the concentration of the cryopreservative until the desired final concentration of cryopreservative is achieved. In preferred embodiments, the cells are contacted with a cryopreservation solution containing the cryopreservative at the desired final concentration or the cryopreservative is added directly to the base medium without a gradual increase in concentration.

The cryopreservation solution includes the cryopreservative in an appropriate base medium. Any type of media can be used for this purpose. For example, any of the hibernation media listed above can be used as the base medium for a cryopreservation solution. In preferred embodiments, the base medium to which the cryopreservative is added is free of added $Ca^{++}$. In certain embodiments the medium to which the cryopreservative is added is free of added protein and/or free of a buffer. In other embodiments, the base medium to which the cryopreservative is added includes or consists of about 0.2–0.9% glucose and about 0.9% NaCl. In preferred embodiments, the base medium to which the cryopreservative is added includes or consists of about 0.35–0.9% glucose and about 0.9% NaCl. In another preferred embodiment, the base medium to which the cryopreservative is added includes or consists of about 0.6% glucose and about 0.9% NaCl. Alternative media can also be used, see e.g., that described by Gage et al. (1985 *Neuroscience Letters* 60:133).

In certain embodiments the cryopreservation solution can also contain added protein, for example, serum, e.g., fetal calf serum or human serum, or a serum protein, e.g., albumin. In other embodiments, the cryopreservative can also contain other additives, such as those described above for inclusion in hibernation media, for example, antioxidants, growth factors, KCl (e.g., at about 30 mM), lactate (e.g., at about 20 mM), pyruvate, $MgCl_2$ (e.g., at about 2–3 mM), sorbitol (e.g., to an osmolarity of about 300 mM) or other additives as are well known in the art (e.g., as taught by Kawamoto and Barrett supra).

Once the cells are suspended in cryopreservation solution, the temperature of the cells is reduced in a controlled manner. In cooling the cells to below freezing, preferably the reduction in temperature occurs slowly to allow the cells to establish an equilibrium between the intracellular and extracellular concentration of cryopreservative such that intracellular ice crystal formation is inhibited. On the other hand, the rate of cooling is preferably fast enough to protect the cells from excess water loss and the toxic effects of cryopreservatives. Controlled freezing may be accomplished with the aid of commercially available electronically controlled freezer equipment, e.g., a Cryomed or Planer Biomed controlled rate freezer. In an exemplary freezing program a cell sample and the freezing chamber are brought to about 1° C. to 9° C., preferably about 4° C. The cells are then cooled at a rate of about 1° C./min to 7° C./min, preferably about 2° C./min. until the cells reach about −6° C. to +6° C., preferably about −1° C. The chamber is brought to about −6° C. to +6° C., preferably about −1° C., and the sample is held at this temperature for about 9–19 minutes, preferably about 14 minutes. The sample is cooled at a rate of about 1° C./minute to 6° C./minute, preferably about 1.2°/minute until the sample reaches about −16° C. to about −6° C., preferably about −11° C. The freezing chamber is subsequently cooled at a rate of about 83 to about 92° C./minute, preferably about 88°/minute until the sample reaches about −22° C. to −32° C., preferably about −27° C. The chamber is warmed to about −38 to about −28° C., preferably about −33° C. and the sample is held for about 5–15 minutes, preferably about 10 minutes. The cells are then cooled at a rate of about 1–5°/minute, preferably about 1°/minute until the sample reaches about −40 to about −50° C., preferably about −45° C. Next, the cells are cooled at about 1–7°/minute, preferably about 2°/minute until the cells reach about −55 to about −65° C., preferably about −60° C. The sample is then cooled at about 1° to about 10°/minute, preferably about 5°/minute until it reaches −90° C.

The cells can then be cryopreserved at a temperature of between −20° C. and about −250° C. Preferably, the cells are stored below −90° C. to minimize the risk of ice recrystalization. In particularly preferred embodiments, the cells are cryopreserved in liquid nitrogen at about −196° C.

Thawing Conditions

After cryopreservation, the cells are preferably thawed rapidly, e.g., by quick immersion in liquid at 37° C. Once the cells are thawed, dilution of the cryopreservative is accomplished by gradual addition of a dilution media. Preferably, the cryopreservative is gradually diluted by a slow multi-step addition of media. For example, cells can be diluted slowly by adding a dilution medium (e.g., a 1:1 dilution) and allowed to sit for 5 minutes at room temperature. The 1:1 dilution can be repeated twice more by slowly adding dilution medium, waiting 5 minutes, and then adding more dilution medium. In other embodiments, a one-step dilution procedure can be used.

Any media can be used for diluting the cryopreservation solution which is in contact with the thawed cells. For example, any of the media listed above for use in hibernating cells can be used for diluting the cryopreservation solution. Other media are also appropriate, for example, Hank's balanced salt solution (preferably without $Ca^{++}$) containing glucose (about 0.6%) can be used. Additives, e.g., as listed above for inclusion in hibernation or freezing media can also be used in media for dilution. Exemplary additives include, for example, buffers (e.g., phosphate buffers, HEPES, or the like) antioxidants, growth factors, KCl (e.g., at about 30 mM), lactate (e.g., at about 20 mM), pyruvate, $MgCl_2$ (e.g., at about 2–3 mM), sorbitol (e.g., to an osmolarity of about 300 mM) or others additives as are well known in the art (e.g., as taught by Kawamoto and Barrett supra). Another suitable additive includes DNase (e.g., commercially available from Genentech, Incorporated as PULMOZYMEOR®). The medium which is used for diluting the cryopreservation solution can, optionally, contain added protein, e.g., added protein (e.g., mammalian serum (preferably heat inactivated) or a serum protein such as albumin (e.g., commercially available from Alpha Therapeutic Corporation)). In other embodiments, the medium contains no added protein and/or no added buffer.

When cells have been frozen as pieces of tissue, the thawed tissue can be dissociated, if desired, into individual cells, using methods known in the art and described supra.

After dilution of the cryopreservative, the cells can then be allowed to settle or a pellet of cells can be formed under centrifugal force in order to remove as much of the cryopreservation solution from the cells as possible. The cells can then be washed in medium which does not contain a cryopreservative. It is preferable for the cells to remain at room temperature after the addition of the wash media and prior to letting the cells settle or form a pellet under centrifugal force. In preferred embodiments, the cells remain at room temperature for at least 15 minutes prior to the second centrifugation. Any medium known in the art can be used to wash the cells, for example, any of the hibernation or dilution media set forth above can be used.

For use in transplantation, cells should be suspended in a final medium which is suitable for administration to a subject. In certain embodiments, the cells are resuspended in a solution including or consisting of glucose (e.g., about 0.2–0.9%) and sodium chloride (e.g., about 0.9%). In preferred embodiments, the cells are resuspended in a solution including or consisting of glucose (e.g., about 0.3–0.6%) and sodium chloride (e.g., about 0.9%). In particularly preferred embodiments, the cells are resuspended in a final solution including or consisting of about 0.35% glucose and about 0.9% saline In addition, the thawed cells may be maintained in hibernation medium as described above at between 0 and 37° C., preferably about 4° C. for up to 3–5 days prior to use in transplantation without a statistically significant loss in viability.

Methods of Determining Viability and/or Functionality of Recovered Cells

After storage, it may be desirable to assay the viability and/or functionality of the cells prior to transplantation to confirm their suitability for use, e.g., in transplantation. This can be accomplished using a variety of methods known in the art. For example, the cells can be stained using vital stains, such as, e.g., trypan blue or ethidium bromide or acridine orange. In certain embodiments, a population of cells suitable for transplantation is at least between about 75–100% viable. In preferred embodiments, a population of cells suitable for transplantation is at least about 80% viable. In particularly preferred embodiments, such a population of cells is at least about 85% viable.

In other embodiments, the morphometric characteristics of the cells can be determined as a measure of the suitability of cells for use in transplantation (see e.g., Petite and Calvet. 1997 *Brain Research* 769:1). In preferred embodiments, the morphology of cells which have been stored using the instant methods and are suitable for transplantation does not differ (e.g., statistically significant) from that of fresh cells. The morphology of the cells and their ability to integrate into the host nervous system can also be tested post-transplantation (Nikkhah et al. 1995 *Brain Research* 687:22). In preferred embodiments, the in vivo morphology of cells which have been stored using the instant methods and are suitable for transplantation does not differ (e.g., statistically significant) from that of fresh cells. Graft volume of transplanted cells can also be measured (Sauer and Brundin. 1991 *Restorative Neurology and Neuroscience* 2:123). In preferred embodiments, the graft volume of cells which have been stored using the instant methods and are suitable for transplantation does not differ (e.g., statistically significant) from that of fresh cells.

Cells which have been stored can also be assayed for the presence of neural cell markers to determine if they are suitable for use in transplantation. For example, methods and reagents useful in detecting the expression of glial fibrillary acidic protein, gamma amino butyric acid (GABA), neuron-specific enolase, tyrosine hydroxylase (TH), norepinephrine, serotonin, 3,4,-dihydroxyphenylacetic acid (DOPAC), homovanillic acid, 5-hydroxyindole acetic acid, acetyl cholinesterase, or other markers are available (see, e.g., Petite and Calvet 1995 *Brain Research* 669:263; Collier et al. 1987 *Brain Research* 436:363; Petite and Calvet 1997 747:279). In preferred embodiments, cells suitable for transplantation display an immunoreactivity pattern, e.g., TH activity, which is not lower (e.g., statistically significant) than that demonstrated in a fresh population of cells.

Additionally, or alternatively, the cells can be tested for their functionality. For example, the ventral mesencephalon cells could be transplanted into 6-OHDA lesioned rats (Kamo et al. 1986 *Brain Research* 397:372). The ability of the cells to reduce pregraft ipsilateral amphetamine-induced motor asymmetry can be tested. In preferred embodiments, a population of cells suitable for transplantation compensates (e.g., statistically significant) for a neural defect in such an in vivo animal model. For example, a population of cells obtained by the instant methods compensates for a 6-OHDA lesion as well as or better than (e.g., statistically significant) a fresh population of cells.

Treatment of Disease

Cells which have been cryopreserved using the instant methods can be used to treat a variety of neurodegenerative diseases or dysfunctions. For example, Parkinson's disease, Huntington's disease, Lou Gehrig's disease or amyotrophic lateral sclerosis, multiple sclerosis, and Alzheimer's disease, have all been linked to the degeneration of neurons in specific locations in the brain or spinal cord. In addition, damage to the nervous system, caused by, for example, stroke, epilepsy, cerebral palsy, spinal cord injury, or chronic pain all result in neuronal loss and can be treated to restore neuronal physiology using cells obtained by the instant methods.

This invention is illustrated further by the following examples which should not be construed as further limiting the subject invention. The contents of all references, published patent applications and patents cited throughout this application are incorporated herein by reference.

EXAMPLE 1

Cryopreservation of Porcine Fetal Ventral Mesencephalic Tissue for Transplantation Donor tissue was obtained from pig fetuses (28 days gestational age) (6–10/litter). After microscopic dissection of the ventral mesencephalon (VM), half of the VM explants were dissociated and prepared as a cell suspension. Half of the cell suspension was used to assess the status of the cells, the culture characteristics of the cells, and the functionality of the cells.

Results

The number of cells harvested was determined and the viability of the harvested cells was determined using acridine orange-ethidium bromide (expressed as the percentage of viable cells with respect to the total number of cells). A portion of this cell suspension was cultured for 5 days, and yet another portion of the cell suspension was stereotatically implanted into 6-hydroxydopamine lesioned rats. The other half of the VM explant cell suspension was stored in a hibernation medium. The hibernation medium consisted of 30 mM KCl, 5 mM glucose, 2.36 mM $MgCl_2$, 10.1 mM $NaH_2PO_4$, 5 mM $NaHPO_4$, and 20 mM lactic acid (pH 7.2). The osmolarity of the solution was measured and sorbitol was added until the osmolarity of the solution reached 300 mM. The cells were hibernated at 4° C. for 44 hours.

Afterwards, the cells were spun down and resuspended in freezing media containing 0.9% saline, 0.6% glucose, and 10% dimethyl sulfoxide solution (at a concentration of approximately $20 \times 10^6$ cells/ml) and put in a programmed freezer within 15 minutes.

The cells and the freezing chamber were brought to 4° C. The cells were then cooled at a rate of 2° C./min. until the cells reached −1° C. The chamber was brought to −1° C., and the sample was held at this temperature for 14 minutes. The sample was cooled at a rate of 1.2°/minute until the sample reached −11°C. The freezing chamber was subsequently cooled at a rate of 88°/minute until the sample reached about −27° C. The chamber was warmed to −33° C. and the sample was held for 10 minutes. The cells were then cooled at a rate of 1°/minute until the sample reached −45° C. Next, the cells were cooled at 2°/minute until the cells reached −60° C. The sample was then cooled 5°/minute until it reached −90° C. After completion of the freezing cycle, the cells were transferred to liquid nitrogen within 90 minutes and stored in liquid nitrogen for a period of time between 2 weeks and 1 year.

At desired times, the tissue was rapidly thawed by transferring the cells to a 37° C. water bath. The cells were transferred to a 15 ml sterile tube and pipetted gently to dissociate. One ml of washing media (containing HBSS without Ca++ or Mg++, 0.6% glucose, 11 mM HEPES, 20% heat inactivated fetal calf serum, and 50 µg/ml DNase) was added to dilute the cells 1:1. The cells were allowed to sit for 5 minutes at room temperature. The 1:1 dilution was repeated two more times by slowly adding 2 ml and 4 ml washing media, respectively, with 5 min waiting between additions. After 5 minutes, the cells were spun down and as much of the DMSO-containing washing media was removed as possible. The cells were resuspended in 1 ml of washing media for viability testing. The cells were allowed to sit at room temperature for at least 15 minutes prior to the second spin to remove DMSO.

The viability after cryopreservation (86.7=2.1%) (n=7) did not differ significantly (p=0.02) from fresh control (86.3=5.8%) (n±7). The total number of living cells per VM explant after cryopreservation ($3.24=0.89\times10^6$ cells NVM) (n=6) was slightly lower, but not significantly (p=0.02) than fresh control ($4.14=1.45\times10^6$ cells/VM)(n=6). The morphology of cultured porcine VM cells after cryopreservation was identical to that of fresh cells. In both groups TH positive neurons constituted only a minor fraction of the total number of cells.

The cells were resuspended to 100,000 cells/$\mu$l in transplantation media (0.9% saline, 0.35% glucose). A portion of the thawed cells were stereotaxically implanted into lesioned rats in the same manner as for the fresh tissue. The rat brains were removed fourteen weeks after implantation. The brains were sectioned and immunostained for tyrosine hydroxylase (TH) in order to investigate survival and outgrowth of the implants, particularly, that of catecholaminergic neurons.

Cryopreservation of porcine fetal VM cells has little or no effect on viability, survival, and outgrowth in vivo after implantation into rat striatum. Thus, cryopreservation proves to be a reliable method of storing fetal VM cells suitable for transplantation.

EXAMPLE 2

Demonstration of Functional Equivalency of Cryopreserved Porcine Fetal Ventral Mesencephalic Tissue.

Donor brains were obtained from pig fetuses (27 days of gestational age) and the ventral mesencephalon was dissected. Tissue was pooled and a single-cell suspension was prepared. Three experimental groups received cells implanted into the corpus striatum of Sprague Dawley rats. These groups included a) freshly isolated cells hibernated for 24 hrs at 4° C. in transplantation media containing 0.35% glucose and 0.9% saline, b) cells cryopreserved for 1 week, and c) cells cryopreserved for 1 month. Stereotaxic transplantation was performed into 6-hydroxydopamine lesioned animals which were prescreened for amphetamine-induced rotation (greater than 7 rotations per minute after 5 mg/kg injection of amphetamine i.p.). The following sterotaxic coordinates relative to Bregma were used: A=+0.5, L=−2.5, V=−5, and −4.2 with the incisor bar set at −2.5. Two 1 $\mu$l injections of 100,000 cells each were deposited. Each experimental group consisted of 13 animals all of which received daily cyclosporine injections to prevent graft rejection. In two groups, 1 animal each dies during the course of the experiment.

All cells were hibernated for 24 hours at 4° C. in transplantation media containing 0.35% glucose and 0.9% saline. Cryopreservation was performed by replacing the hibernation media with 1 ml freezing media containing 0.6% glucose, 0.9% saline, and 10% DMSO. $10\times10^6$ cells were frozen per vial using the freezing program described in Example 1. Frozen cells were stored in the vapor phase of liquid nitrogen.

Cells were thawed by removing the cryovial from liquid nitrogen and placing the tube in a 37° C. water bath until all ice crystals melted. The cells were then diluted with three 1:1 dilutions of wash media (HBSS without Ca+2 or Mg+2, 0.6% glucose, 1% human serum albumin, 50 mg/ml DNase). Each dilution was separated by 5 minutes at room temperature. The cells were then centrifuged for 7 minutes at 1,000 rpm and the pellet was resuspended in 1 ml wash media and allowed to sit for 15 minutes at room temperature. The cells were again centrifuged as above and resuspended in transplantation media (0.35% glucose, 0.9% saline) at 100,000 cells/ml. All viability and cell recovery calculations were performed using acridine orange-ethidium bromide staining.

At the end of 14 weeks, animals were sacrificed and perfused. Coronal sections were stained to determine the level of surviving tyrosine hydroxylase positive neurons and the amount of cellular immune response.

Using this transplantation paradigm, graft functionality is measured by determining the level of correction of drug-induced rotation. As the graft matures and integrates in the host brain, ipsilateral rotation decreases until animals experience close to no rotational behavior during the testing.

Results

VM cells after isolation and hibernation for 24 hrs at 4° C. had in vitro viabilities of 91%. Cryopreserved cells were thawed at either 1 week or 4 weeks had in vitro viabilities of 82% and 88% respectively. Beginning 6 weeks after transplantation, animals were tested every two weeks for amphetamine-induced rotation. Correction of drug-induced rotation was evident between 6–10 weeks in animals with surviving grafts and was consistent over 14 weeks post-implantation at which time the animals were sacrificed. In the first group of animals which received cells hibernated cells for 1 day prior to transplantation, rotational recovery was observed in 12 out of 13 animals. The animal which lacked rotational recovery in this group and three of the animals which did demonstrate rotational recovery showed evidence of significant chronic rejection. In the second group, animals received cells which had been cryopreserved for 1 week. Rotational correction was observed in 10 out of 12 animals. In the two animals that lacked rotational correction, there was evidence of chronic rejection. Finally, in the third group which received cells that were frozen for 4 weeks, rotational correction was observed in 9 out of 12 animals. The animals which lacked roational recovery in this group and one other animal which did demonstrate rotational recovery showed evidence of significant chronic rejection.

Thus, animals transplanted with 24 hour hibernated cells, 1 week cryopreserved cells, and 4 week cryopreserved cells, contained 69%, 83%, and 66%, healthy grafts after 14 weeks post transplantation. Thus, cryopreserved cells apear to have equivalent functionality to cells which are hibernated for 24 hrs at 4° C. prior to transplantation.

EXAMPLE 3

In order to determine critical variables which affect cryopreservation of fetal porcine neural cells, a number of variations have been made to the protocol described in Example 1. Shown in Table 1 are the relative effects of changing certain individual variables and comparing these results to those obtained using the protocol of Example 1. The results obtained using the protocol of Example 1 are labeled as 'control' in the table below. The effects are based on measuring in vitro viability and recovery of viable cells after hibernation and cryopreservation.

TABLE I

| Cell Type | Effect |
| --- | --- |
| ventral mesencephalon | Control Cells |
| lateral ganglionic eminence | Equivalent |
| cortex | Detrimental |
| Hibernation Media | |
| Complex hibernation media described in Example 1 | Control Media |
| 0.35% glucose, 0.9% saline | Equivalent |
| Freezing | |
| Freezing media described in Example 1 containing 10% DMSO | Control Conditions |
| Freezing media described in Example 1 containing 7% DMSO | Equivalent |
| Slower addition of DMSO (step-wise addition of DMSO every 2 minutes at room temperature to give concentration of 0.5%, 1%, 2%, 4% 7% then 10%) | Improvement |
| Incubation of cells in freezing media containing DMSO for 5 minutes at room temperature or 40 minutes at 4° C. prior to freezing cells | No Change |
| Steady temperature decrease at 1° C./minute from 4° C. to −90° C. | Detrimental |
| Steady temperature decrease at 1° C./minute from 4° C. to −5° C. and 0.3° C./minute from −5 to −90° C. | Detrimental |
| Thaw | |
| Thaw in 37° C. waterbath | Control Thaw |
| Thaw in waterbaths at 0° C., 5° C., 10° C., or room temperature | No Change |
| Thaw by placing tube at room temperature | No Change |
| Dilution of Cryoprotectant | |
| Wash buffer described in Example 1 (WB) | Control Buffer |
| Wash buffer in which bovine serum is replaced by human serum albumin (HSA) | No Change |
| Wash buffer without added protein or serum | Variable results |
| Wash buffer without HEPES buffer containing HSA | No Change |
| Dilution of DMSO in three 1:1 dilution steps at room temperature | Control Dilution |
| Rapid dilution of DMSO | Detrimental |
| Dilution of DMSO in three 1:1 dilution steps at 4° C. | Detrimental |
| Fixed molar dilution of cryoprotectant[1] | Improvement |
| Dilution of cells in hypertonic buffers containing salt or sucrose | Detrimental |

[1]Fixed molar dilution involved using the same wash buffer but rather than diluting cryoprotectant concentration in half three times (net effect is dropping from 10% DMSO to 5% then 2.5% then 1.25%) the concentration of DMSO is decreased more evenly in seven steps each step dropping the DMSO concentration 0.9% every 1 minute.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A method for storing a population of human or porcine neural cells suitable for transplantation comprising:
    a) contacting a population of human or porcine neural cells with a hibernation medium free of $Ca^{++}$ and free of protein and free of buffer to thereby produce a cell suspension; and
    b) maintaining the cell suspension at about 4° C. for between at least about 12–72 hours to thereby store a population of neural cells suitable for transplantation, wherein the population of neural cells is between at least about 75–100% viable.

2. A method for storing a population of human or porcine neural cells suitable for transplantation comprising:
    a) contacting a population of human or porcine neural cells with a hibernation medium free of buffer to thereby produce a cell suspension; and
    b) maintaining the cell suspension at about 4° C. for between at least about 12–72 hours to thereby store a population of neural cells suitable for transplantation, wherein the population of neural cells is between at least about 75–100% viable.

3. A method for storing a population of human or porcine neural cells suitable for transplantation comprising:
    a) contacting a population of human or porcine neural cells with a hibernation medium which medium is free of protein and free of a buffer to thereby produce a cell suspension; and
    b) maintaining the cell suspension at about 4° C. for between at least about 12–72 hours to thereby store a population of neural cells suitable for transplantation, wherein the population of neural cells is between at least about 75–100% viable.

4. A method for storing a population of human or porcine neural cells suitable for transplantation comprising:
    a) contacting a population of human or porcine neural cells with a hibernation medium which is free of buffer and consists of glucose and sodium chloride to thereby produce a cell suspension; and
    b) maintaining the cell suspension at about 4° C. for between at least about 12–72 hours to thereby store a population of neural cells suitable for transplantation, wherein the population of neural cells is between at least about 75–100% viable.

5. A method for cryopreserving a population of human or porcine neural cells suitable for transplantation comprising:
    a) contacting a population of human or porcine neural cells with a cryopreservation solution which is free of a buffer and which comprises a cryopreservative to thereby obtain a population of cells for cryopreservation; and b) decreasing the temperature of the population of neural cells to about −196° C. to thereby cryopreserve a population of neural cells suitable for transplantation, wherein population of neural cells is between at least about 75–100% viable.

6. A method for cryopreserving a population of human or porcine neural cells suitable for transplantation comprising:

a) contacting a population of human or porcine neural cells with a cryopreservation solution which is free of protein and free of buffer and which comprises a cryopreservative to thereby obtain a population of cells for cryopreservation; and b) decreasing the temperature of the population of neural cells for cryopreservation to about −196° C. to thereby cryopreserve a population of neural cells suitable for transplantation, wherein the population of neural cells is between at least about 75–100% viable.

7. A method for cryopreserving a population of human or porcine neural dells suitable for transplantation comprising:

a) contacting a population of human or porcine neural cells with a cryopreservation solution consisting of glucose, sodium chloride, and a cryopreservative to thereby obtain a population of cells for cryopreservation; and b) decreasing the temperature of the population of neural cells for cryopreservation to about −196° C. to thereby cryopreserve a population of neural cells suitable for transplantation, wherein the population of neural cells is between at least about 75–100% viable.

8. A method of obtaining a population of human or porcine neural cells suitable for transplantation comprising:

a) contacting a population of human or porcine neural cells with a cryopreservation solution free of a buffer and comprising a cryopreservative to thereby obtain a population of cells for cryopreservation;

b) decreasing the temperature of the population of neural cells for cryopreservation to about −196° C. to obtain cryopreserved neural cells; and c) increasing the temperature of the cryopreserved neural cells to thereby obtain a population of neural cells suitable for transplantation, wherein the population of neural cells is between at least about 75–100% viable.

9. A method of obtaining a population of human or porcine neural cells suitable for transplantation comprising:

a) contacting a population of human or porcine neural cells with a cryopreservation solution free of protein and free of buffer and which comprises a cryopreservative to thereby produce a population of neural cells suitable for cryopreservation;

b) decreasing the temperature of the population of neural cells for cryopreservation to about −196° C. to obtain cryopreserved neural cells; and c) increasing the temperature of the cryopreserved neural cells to thereby obtain a population of neural cells suitable for transplantation, wherein the population of neural cells is between at least about 75–100% viable.

10. A method of obtaining a population of human or porcine neural cells suitable for transplantation comprising:

a) contacting a population of human or porcine neural cells with a cryopreservation solution consisting of: glucose, sodium chloride, and a cryopreservative to thereby obtain a population of cells for cryopreservation;

b) decreasing the temperature of the population of neural cells for cryopreservation to about −196° C. to obtain cryopreserved neural cells; and c) increasing the temperature of the cryopreserved neural cells to thereby obtain a population of neural cells suitable for transplantation, wherein the population of neural cells is between at least about 75–100% viable.

11. The method of claim 8, 9, or 10, wherein the neural cells are fetal human cells.

12. The method of claim 11, wherein the neural cells are differentiated from human neural stem or neural progenitor cells that have been induced to differentiate in vitro.

13. The method of claim 8, 9, or 10 wherein the neural cells are porcine cells.

14. The method of claim 13, wherein the porcine neural cells are ventral mesencephalic cells.

15. The method of claim 13, wherein the porcine neural cells are spinal cord cells.

16. The method of claim 13, wherein the porcine neural cells are striatal cells.

17. The method of claim 13, wherein the porcine neural cells are cortical cells.

18. A method for storing a population of human or porcine neural cells suitable for transplantation comprising:

a) contacting a population of human or porcine neural cells with a hibernation medium which is free of buffer to thereby produce a cell suspension;

b) maintaining the cell suspension for at least about 24 hours at about 4° C. in hibernation medium; and c) contacting the cell suspension with a cryopreservation solution to thereby store a population of neural cells suitable for transplantation, wherein the population of neural cells is between at least about 75–100% viable.

19. A method for cryopreserving a population of human or porcine neural cells suitable for transplantation comprising:

a) contacting a population of human or porcine neural cells with a hibernation medium which is free of buffer to thereby produce a cell suspension;

b) maintaining the cell suspension for at least about 24 hours at about 4° C. in hibernation medium;

c) contacting the cell suspension with a cryopreservation solution to thereby obtain a population of cells for cryopreservation; and d) decreasing the temperature of the population of neural cells suitable for cryopreservation to about −196° C. to thereby cryopreserve a population of neural cells suitable for transplantation, wherein the population of neural cells is between at least about 75–100% viable.

20. A method of obtaining a population of human or porcine neural cells for transplantation comprising:

a) contacting a population of human or porcine neural cells with a hibernation medium which is free of buffer to thereby produce a cell suspension;

b) maintaining the cell suspension for at least about 24 hours at about 4° C. in hibernation medium;

c) contacting the cell suspension with a cryopreservation solution to thereby obtain a population of cells for cryopreservation;

d) decreasing the temperature of the population of neural cells for cryopreservation to about 196° C.; and e) increasing the temperature of the neural cells to thereby obtain population of neural cells suitable for transplantation, wherein the population of neural cells is between at least about 75–100% viable.

* * * * *

UNITED STATES PATENT AND TRADEMARK OFFICE
CERTIFICATE OF CORRECTION

PATENT NO. : 6,713,245 B2
DATED : March 30, 2004
INVENTOR(S) : Jan Koopmans et al.

It is certified that error appears in the above-identified patent and that said Letters Patent is hereby corrected as shown below:

Column 20,
Line 50, "...of neural cells for cryopreservation to about 196°C.;" should be
-- of neural cells for cryopreservation to about -196°C.; --

Signed and Sealed this

Sixth Day of July, 2004

JON W. DUDAS
*Acting Director of the United States Patent and Trademark Office*